Sept. 18, 1962 C. B. THOMAS Plant Pat. 2,172
WATER LILY PLANT
Filed Oct. 23, 1961 2 Sheets-Sheet 1
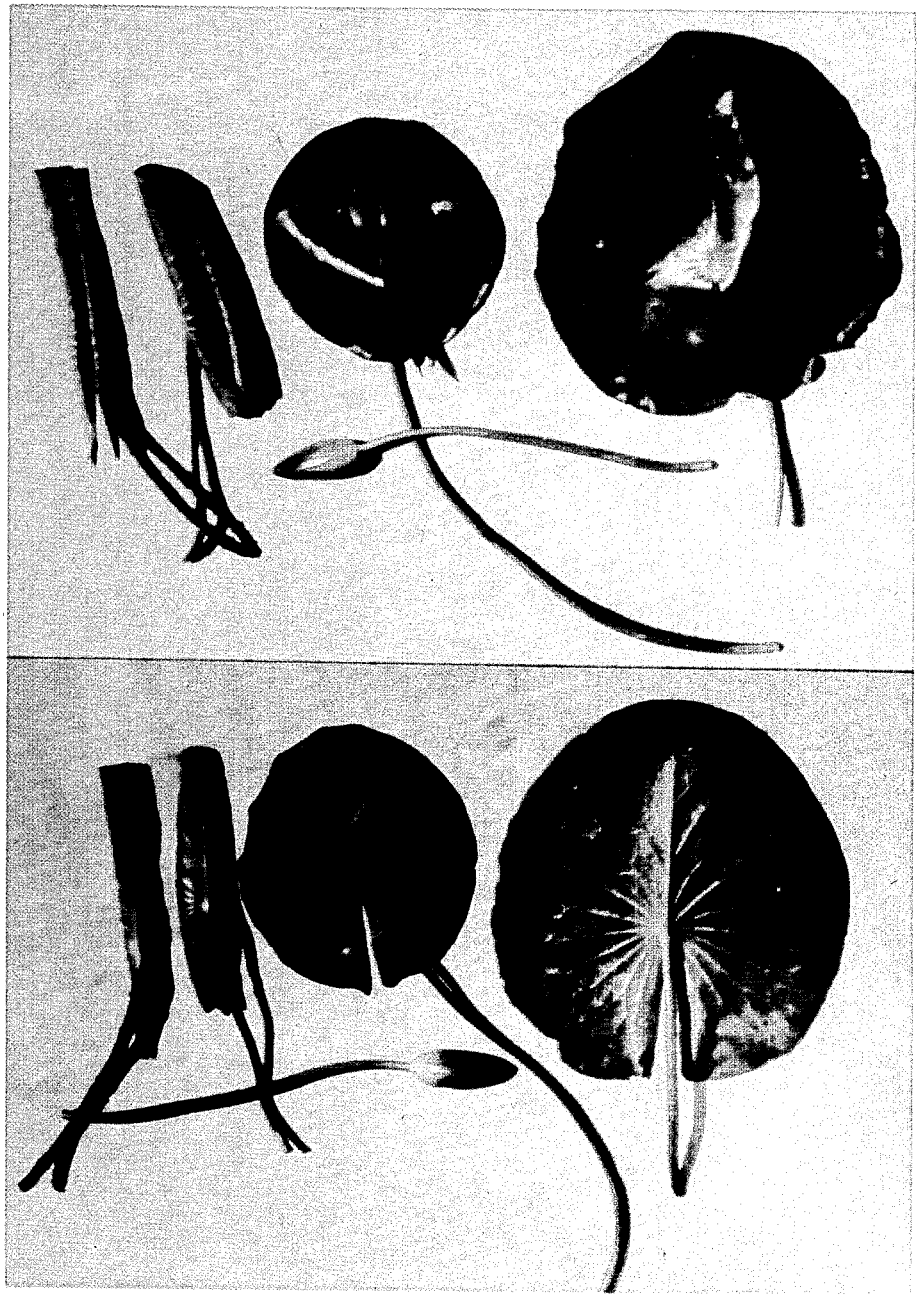
INVENTOR
Charles Brosius Thomas
BY Robb & Robb
ATTORNEYS Sept. 18, 1962 C. B. THOMAS Plant Pat. 2,172
WATER LILY PLANT
Filed Oct. 23, 1961 2 Sheets-Sheet 2
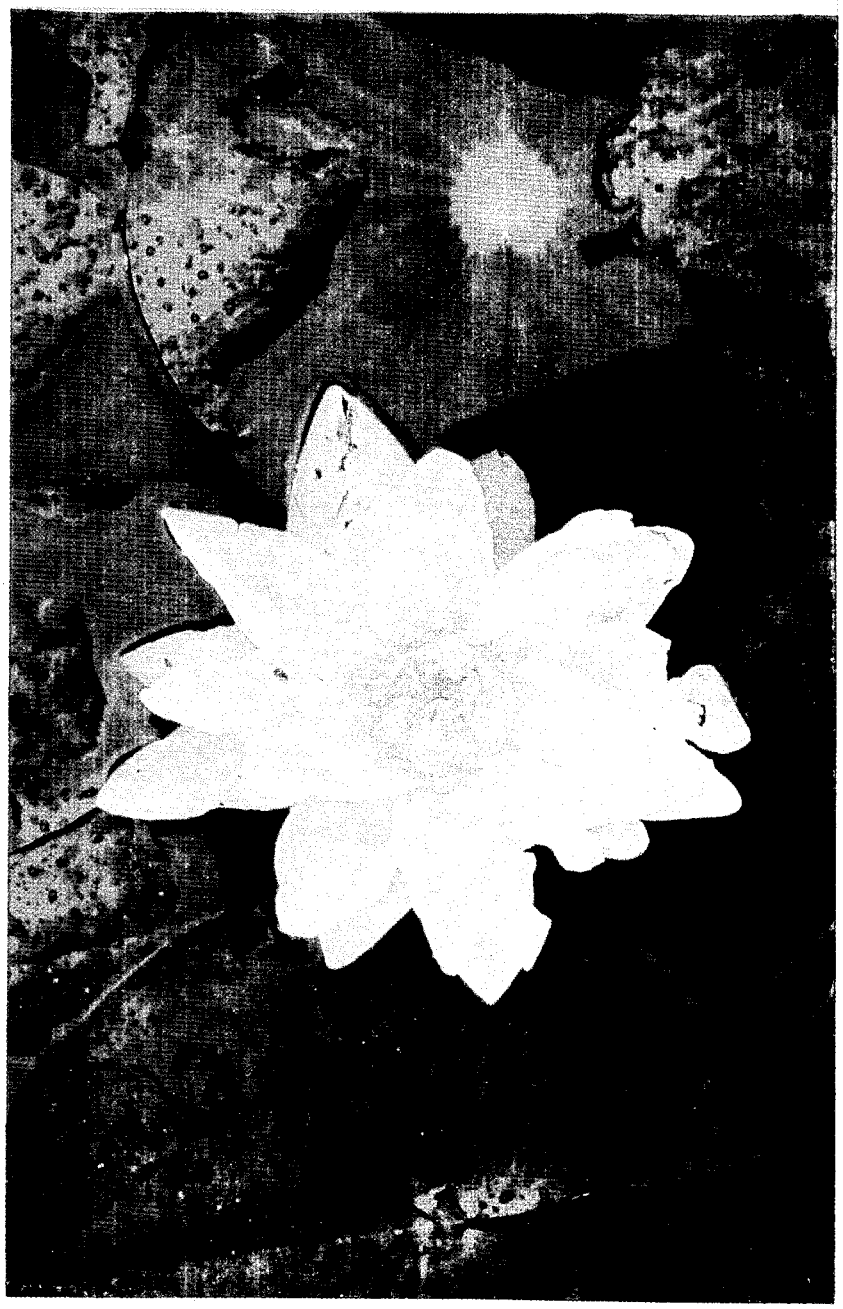
INVENTOR
Charles Brosius Thomas
BY Robb & Robb
ATTORNEYS United States Patent Office Plant Pat. 2,172
Patented Sept. 18, 1962

2,172
WATER LILY PLANT

Charles Brosius Thomas, Lilypons, Md.

Filed Oct. 23, 1961, Ser. No. 147,114
1 Claim. (Cl. 47—60)

The present invention relates to a new and distinct variety of water lily plant which was originated by me by crossing the variety known as "Sunrise" (unpatented) with the variety known as "Gladstone" (unpatented).

As the result of this breeding, I have produced a new variety of water lily plant which is unique and distinct from all other varieties of which I am aware, as evidenced by the following combination of outstanding characteristics which are present in the new variety and which distinguish it from its parents, as well as from all other varieties:

(1) Reliable growth;
(2) Large size of the flowers;
(3) Star-shaped form of the flowers; and
(4) A distinctive and attractive white general color tonality of the flowers.

In comparison with the parent variety "Sunrise," my new water lily plant bears white flowers rather than the yellow colored flowers of this parent.

As compared with the parent variety "Gladstone," the flowers of my new variety are star-shaped rather than cup-shaped.

Asexual reproduction of my new water lily plant by rhizome division, as performed by me at Lilypons, Maryland, shows that the foregoing characteristics and distinctions are fixed and come true, and are transmissible through succeeding propagations.

The accompanying drawings show typical specimens of the flowers and foliage of my new variety in different stages of development and as depicted in color as nearly true as it is reasonably possible to make the same in a color illustration of this character, with both the upper and under surfaces of main leaf specimens and two curled submerged leaf specimens being shown.

The following is a detailed description of my new water lily plant, as based upon observations of specimens grown in ponds at Lilypons, Maryand, with color terminology in accordance with general color terms of ordinary dictionary significance:

Parentage: Seedling of "Sunrise" × "Gladstone."
Propagation: Holds its distinguishing characteristics through succeeding propagations by rhizome division.

*Plant*

Foliage:
- *Submerged leaves.*—Shape—round; curled. Length (from petiole to sinus)—2½ inches. Color: upper side—light green; under side—light green with red spots.
- *Main floating leaves.*—Shape—generally round, but slightly elongated. Length (from petiole to sinus)—3½ inches. Color—green.
- *Mature leaves.*—Shape—generally round, but slightly elongated. Size—9 inches. Color: upper side—green; under side—almost red as the result of the spreading of the earlier red spots. Leaf stem: color—light green; length—about 24 inches, depending on growing conditions.

*Flower*

Bloom:
- *Blooming habit.*—From late May through latter part of September.
- *Shape.*—Star-shaped.
- *Color.*—Outer petals—white. Inner petals—yellowish white.
- *Size.*—6½ inches.
- *Number of days open.*—4 days.
- *Number open at one time.*—1 or 2.
- *Distance standing out of water.*—From 1½ to 2 inches.
- *Fragrance.*—Sweet. Nature—spice.

Buds:
- *Shape.*—Normal for star-shaped water lily.
- *Color.*—Light green.

Scape: Color—white.

Sepals:
- *Number.*—4.
- *Color.*—Light brownish-green.
- *Length.*—2½ inches.
- *Width.*—1⅛ inches.
- *Texture.*—Smooth.

Petals:
- *Number.*—27.
- *Length.*—2¾ inches.
- *Width.*—1¼ inches.
- *Color.*—White, with innermost petals being yellowish.

Stamens:
- *Number.*—74.
- *Length.*—Outer—1¾ inches. Inner—⅜ inch.
- *Appendages.*—With.

Carpels:
- *Number.*—11.
- *Length.*—⅜ inch.
- *Color.*—Yellow.

Stigma: Color—yellow.
Lasting quality: Very good.
Shipping quality: Very good.

*Fruit*

Shape: Basically cylindrical, but with middle portion being of slightly larger diameter.
Size:
- *Height.*—½ inch.
- *Width.*—½ inch.

Seeds: Present; fertile.

I claim:

A new and distinct variety of water lily plant, substantially as herein shown and described, characterized particularly as to novelty by the unique combination of reliability of growth, large star-shaped flowers, and an attractive and distinctive white general color tonality of the flowers.

No references cited.